United States Patent
Ott et al.

(10) Patent No.: US 6,632,968 B2
(45) Date of Patent: Oct. 14, 2003

(54) METHOD FOR THE PRODUCTION OF AMINES FROM EPOXIDIZED OLEFINS

(75) Inventors: Christian Ott, Speyer (DE); Marco Bergemann, Hockenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/182,895

(22) PCT Filed: Feb. 16, 2001

(86) PCT No.: PCT/EP01/01783

§ 371 (c)(1), (2), (4) Date: Aug. 2, 2002

(87) PCT Pub. No.: WO01/60782

PCT Pub. Date: Aug. 23, 2001

(65) Prior Publication Data

US 2003/0028053 A1 Feb. 6, 2003

(30) Foreign Application Priority Data

Feb. 18, 2000 (DE) .......................... 100 07 554

(51) Int. Cl.$^7$ .............................. C07C 209/16
(52) U.S. Cl. ....................... 564/475; 564/474
(58) Field of Search ................. 564/474, 475

(56) References Cited

U.S. PATENT DOCUMENTS 4,159,996 A 7/1979 Love et al.
5,810,894 A * 9/1998 Dever et al. .................. 44/412
6,140,541 A * 10/2000 Melder et al. .............. 564/475

FOREIGN PATENT DOCUMENTS

WO 97 44366 11/1997

OTHER PUBLICATIONS

Database CAPLUS on STN, Acc. No. 1991:448842, Koyama et al., JP 03041056 (abstract).*

* cited by examiner

*Primary Examiner*—Brian Davis
(74) *Attorney, Agent, or Firm*—Oblon, Spivak, McClelland, Maier & Neustadt, P.C.

(57) ABSTRACT

A process for preparing amines comprises reacting an epoxide of the formula (I)

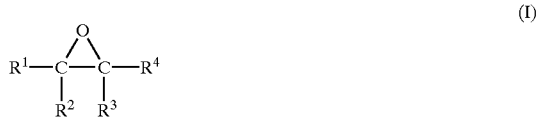

where $R^1$, $R^2$, $R^3$ and $R^4$ are each, independently of one another, hydrogen or a linear or branched, saturated or unsaturated $C_2$–$C_{200}$-hydrocarbon radical, with ammonia and hydrogen in the presence of a catalyst, where the molar ratio of ammonia:epoxide is from 5:1 to 500:1 and the hydrogen pressure is from 10 bar to 500 bar.

10 Claims, No Drawings

METHOD FOR THE PRODUCTION OF AMINES FROM EPOXIDIZED OLEFINS

This application is a 371 of PCT EP01/01783 filed Feb. 16, 2001.

The present invention relates to a process for preparing amines from epoxidized olefins.

Amines are important intermediates for the chemical and pharmaceutical industry. Amines are usually prepared by reaction of alkyl halides with ammonia, by addition of ammonia onto olefinic double bonds, by aminative hydrogenation of aldehydes and ketones, by catalytic hydrogenation of carboxylic acid nitrites and by catalytic reduction of nitroalkanes by means of hydrogen; cf. Ullmann's Encyclopädie der Technischen Chemie, 4th edition 1974, Volume 7, page 375.

WO 97/44 366 describes a process for preparing polyalkenamines by reacting a polyalkene epoxide with an amine and dehydrating and reducing the resulting amino alcohol to give the polyalkenamine. The polyalkene epoxides used are derived from polyalkenes having a number average molecular weight of from at least about 175 to 40,000. The preferred polyalkene is polyisobutene having a number average molecular weight of from about 200 to 3000.

It is an object of the present invention to provide a process for preparing low molecular weight alkylamines from epoxidized low molecular weight olefins.

We have found that this object is achieved by a process for preparing amines, which comprises reacting an epoxide of the formula (I)

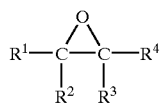

where $R^1$, $R^2$, $R^3$ and $R^4$ are each, independently of one another, hydrogen or a linear or branched, saturated or unsaturated $C_2$–$C_{200}$-hydrocarbon radical, with ammonia and hydrogen in the presence of a catalyst, where the molar ratio of ammonia:epoxide is from 5:1 to 500:1 and the hydrogen pressure is from 10 bar absolute to 500 bar absolute. The radicals $R^1$, $R^2$, $R^3$ and $R^4$ are each, independently of one another, hydrogen or a linear or branched, saturated or unsaturated $C_2$–$C_{200}$-hydrocarbon radical. Preference is given to saturated hydrocarbon radicals, in particular linear saturated hydrocarbon radicals. Among these hydrocarbon radicals, preference is given to $C_2$–$C_{50}$-hydrocarbon radicals, in particular $C_2$–$C_{30}$-hydrocarbon radicals. Examples are n-ethyl, n-propyl, n-butyl, n-pentyl, n-hexyl, n-heptyl, n-octyl, n-nonyl and n-decyl.

The epoxides of the formula (I) are obtained from the corresponding olefins by epoxidation. The epoxidation is carried out, for example, by dissolving the olefin in a suitable solvent, for example diethyl ether or another dipolar aprotic solvent or a nonpolar solvent such as xylene or toluene, drying this solution if appropriate, adding the epoxidizing agent and carrying out the epoxidation at room temperature or with slight heating, for example to about 30–100° C. Examples of epoxidizing agents are peracids, e.g. performic acid, peroxybenzoic acid, m-chloroperoxybenzoic acid or peroxyacetic acid and the peracids formed from $H_2O_2$ and appropriate carboxylic acids, or alkyl peroxides, e.g. tert-butyl hydroperoxide, with preference being given to m-chloroperbenzoic acid and peroxyacetic acid.

In one embodiment of the process of the present invention, $R^1$ is a hydrocarbon radical and $R^2$, $R^3$ and $R^4$ are each a hydrogen atom. Preferred radicals $R^1$ are $C_2$–$C_{50}$-hydrocarbon radicals, particularly preferably $C_2$–$C_{30}$-hydrocarbon radicals. Among these, particular preference is given to the linear, in particular the linear saturated, hydrocarbon radicals. Olefin epoxides used as starting materials in this embodiment of the process of the present invention are, for example, 1-butene epoxide, 1-hexene epoxide, 1-octene epoxide, 1-decene epoxide, 1-dodecene epoxide, 1-tetradecene epoxide, 1-hexadecene epoxide, 1-octadecene epoxide and the epoxidized methyl esters of rapeseed oil acids. In this embodiment, the main product of the reaction is a 1,2-diamine of the formula (II)

$$HR^1(NH_2)C\text{—}C(NH_2)H_2 \qquad (II)$$

In a further embodiment of the process of the present invention, the radicals $R^1$ and $R^2$ are each a hydrocarbon radical and $R^3$ and $R^4$ are each a hydrogen atom. The main product of the reaction in this embodiment is a 1-monoamine of the formula (III):

$$HR^1R^2C\text{—}C(NH_2)H_2 \qquad (III)$$

In a further embodiment of the process of the present invention, $R^1$, $R^3$ and $R^4$ are each a hydrocarbon radical and $R^2$ is a hydrogen atom. The main product of the reaction in this embodiment is a monoamine of the formula (IV):

$$HR^1(NH_2)C\text{—}CR^3R^4H \qquad (IV)$$

In a first preferred embodiment, the conversion of the epoxide (I) into the amine is carried out in one step in which the epoxide (I) is reacted with ammonia in the presence of hydrogen and a catalyst which simultaneously displays both dehydration and hydrogenation properties. This single-stage reaction is preferably employed for preparing the 1,2-diamines (II).

In a second preferred embodiment, the conversion of the epoxide (I) into the amine is carried out in two stages by firstly reacting the epoxide (I) with ammonia in the presence of an alkoxylation catalyst to form the amino alcohol and, if necessary, separating off unreacted reactants. The amino alcohol is hydrogenated in a second stage in the presence of a catalyst which possesses both dehydration and hydrogenation properties to give the amine. This second process variant is particularly useful for preparing monoamines of the formulae III and IV.

The catalyst having dehydration and hydrogenation properties which can be employed according to the present invention is preferably selected from among zeolites and porous oxides of Al, Si, Ti, Zr, Nb, Mg and/or Zn, acidic ion exchangers and heteropolyacids, which each further comprise at least one hydrogenation metal. As hydrogenation metal, preference is given to using Ni, Co, Cu, Fe, Pd, Pt, Ru, Rh or combinations thereof.

Zeolites which can be used according to the present invention are, for example, acidic zeolitic solid catalysts as are described in EP 0 539 821, which is hereby incorporated by reference. Examples of suitable zeolites are zeolites having a mordenite, chabasite or faujasite structure; zeolites of the A, L, X and Y types; zeolites of the pentasil type having an MFI structure; zeolites in which aluminum and/or silicon are wholly or partly replaced by other atoms, e.g. aluminosilicate, borosilicate, iron silicate, beryllium silicate, gallium silicate, chromium silicate, arsenic silicate, antimony silicate and bismuth silicate zeolites or mixtures thereof and also aluminogermanate, borogermanate, gallium germanate and iron germanate zeolites or mixtures thereof or titanium silicate zeolites, e.g. TS-1, ETS 4 and ETS 10.

To optimize selectivity, conversion and operating life, the zeolites used according to the present invention can be doped in an appropriate manner with further elements, as is described, for example, in EP 0 539 821.

In the same way, the zeolites may be doped with the abovementioned hydrogenation metals. The hydrogenation metal should be present in an amount, calculated as oxide, of from 1 to 10% by weight, based on the total weight of the catalytically active composition.

Further suitable catalysts having dehydration and hydrogenation properties are acidic oxides of the elements Al, Si, Zr, Nb, Mg or Zn or mixtures thereof which are doped with at least one of the abovementioned hydrogenation metals. The oxide (calculated as $Al_2O_3$, $SiO_2$, $Nb_2O_5$, MgO or ZnO) is present in a proportion of from about 10 to 99% by weight, preferably from about 40 to 70% by weight, in the catalyst composition (i.e. catalytically active composition). The hydrogenation metal (calculated as NiO, CoO, CuO, $Fe_2O_3$, PdO, PtO, $RuO_2$ or $Rh_2O_3$) is present in a proportion of from about 1 to 90% by weight, preferably from about 30 to 60% by weight, based on the total weight of the catalyst composition. In addition, small amounts, i.e. from about 0.1 to about 5% by weight (calculated for the oxides) of further elements, e.g. Mo or Na, may be present in the oxides used according to the present invention in order to improve catalytic properties such as selectivity and operating life.

Oxides of this type and their preparation are described, for example, in EP 0 696 572, which is hereby incorporated by reference. They are preferably prepared by firstly preparing an aqueous salt solution containing the abovementioned catalyst components and coprecipitating these components by addition of a mineral base, e.g. sodium carbonate, with or without gentle heating. The precipitate is separated off, washed, dried and calcined, e.g. by heating at 500° C. for 4 hours.

The above-described zeolites and active oxides which can be used according to the present invention may, if desired, be conditioned by, if necessary, milling them to a particular particle size and pressing/extruding them to form extrudates or pellets, if appropriate with addition of shaping aids such as graphite.

According to the present invention, particular preference is given to the use of a catalyst which comprises, based on the total weight of the catalytically active composition, about 30% by weight of Zr, calculated as $ZrO_2$,
about 50% by weight of Ni, calculated as NiO,
about 18% by weight of Cu, calculated as CuO,
about 1.5% by weight of Mo, calculated as $MoO_3$ and
about 0.5% by weight of Na, calculated as $Na_2O$.

Alkoxylation catalysts which are, according to the present invention, preferably added to the reaction mixture promote the opening of the epoxide ring. Examples of suitable alkoxylation catalysts are water and alcohols, e.g. methanol or ethanol, mineral acids and carboxylic acids.

In both of the above-described process variants, which can be carried out either continuously or batchwise, the epoxides are reacted at a reaction temperature of from about 100 to 300° C., preferably from about 150 to 250° C., in particular from about 180 to 220° C., and a hydrogen pressure of generally from 10 bar to 500 bar, preferably from 50 bar to 300 bar, in particular about 250 bar. Ammonia is used in a molar ratio to the epoxide of from 5:1 to 500:1, preferably from 10:1 to 500:1, particularly preferably from 20:1 to 250:1. The reaction time is generally from 1 hour to 48 hours, preferably from 1 hour to 24 hours, particularly preferably from 4 hours to 24 hours, in particular about 12 hours. The reaction can be carried out either in bulk or in the presence of a solvent, for example hydrocarbons such as hexane or THF, preferably in this way. A preferred solvent is THF.

The process of the present invention gives high conversions and displays a high selectivity. Thus, in the preparation of 1,2-diamine (II) from 1-olefin epoxides such as 1-epoxydecane, 1-epoxydodecane, 1-epoxytetradecane and 1-epoxyhexadecane, the yield of 1,2-diamine is at least 80 mol % preferably at least 85 mol %, particularly preferably at least 90 mol %. Small amounts of 1-monoamines, secondary amines, secondary amino alcohols and piperazines are formed as by-products.

In the preparation of 1-monoamines (III), yields of at least 68 mol %, preferably at least 82 mol %, are obtained; in the preparation of monoamines (IV), yields of at least 71 mol %, preferably at least 78 mol %, are obtained.

The invention is illustrated by the following examples.

EXAMPLES 1–5

150 g of the epoxide together with 100 g of catalyst H1/88 and 800 ml of THF are placed in an autoclave. The autoclave is flushed twice with 5 bar of nitrogen, and 500 ml of ammonia are then injected at room temperature. 50 bar of hydrogen are subsequently injected at room temperature and the autoclave is heated to 200° C. When the temperature of 200° C. has been reached, further hydrogen is injected until the pressure is 250 bar. The mixture is stirred at 200° C. for 12 hours. The reactor is then cooled to 30° C. and carefully vented. The reaction mixture is heated to 40° C. again and stirred for another 1 hour. The autoclave is finally flushed with 10 bar of nitrogen and cooled to room temperature. The contents of the reactor are filtered and evaporated on a rotary evaporator.

The results of the experiments are summarized in the table.

| Epoxide | Main product | Yield [mol %] | By-products (in mol %) |
|---|---|---|---|
| Epoxidized methyl esters of rapeseed oil acids | 9,10-Diaminostearamide | 68 | 9,10,12,13-tetraaminostearamide (20%) 9,10,12,13,15,16-hexaaminostearamide (9%) |
| 1-Epoxydecane | 1,2-Diaminodecane | 81 | Bis(2-hydroxydecyl)amine (10%) 2,5- and 2,6-bis(octyl)piperazine (7%) |
| 1-Epoxydodecane | 1,2-Diaminododecane | 87 | Bis(2-hydroxydodecyl)amine (3%) 2,5- and 2,6-bis(decyl)piperazine (4%) |

-continued

The results of the experiments are summarized in the table.

| Epoxide | Main product | Yield [mol %] | By-products (in mol %) |
| --- | --- | --- | --- |
| 1-Epoxytetradecane | 1,2-Diaminotetradecane | 93 | Bis(2-hydroxytetradecyl)amine (3%) 2,5- and 2,6-bis(dodecyl)piperazine (1.5%) |
| 1-Epoxyhexadecane | 1,2-Diaminohexadecane | 96 | Bis(2-hydroxyhexadecyl)amine (1.5%) 2,5- and 2,6-bis(tetradecyl)piperazine (1%) |

We claim:

1. A process for preparing amines, which comprises reacting an epoxide of the formula (I)

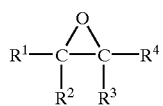 (I)

where $R^1$, $R^2$, $R^3$ and $R^4$ are each, independently of one another, hydrogen or a linear or branched, saturated or unsaturated $C_2$–$C_{200}$-hydrocarbon radical, with ammonia and hydrogen in the presence of a catalyst, where the molar ratio of ammonia:epoxide is from 5:1 to 500:1 and the hydrogen pressure is from 10 bar to 500 bar.

2. A process as claimed in claim 1, wherein $R^1$ is a hydrocarbon radical and $R^2$, $R^3$ and $R^4$ are each a hydrogen atom and the main product of the reaction is a 1,2-diamine of the formula (II)

$$HR^1(NH_2)C\text{—}C(NH_2)H_2 \qquad (II).$$

3. A process as claimed in claim 1, wherein $R^1$ and $R^2$ are each a hydrocarbon radical and $R^3$ and $R^4$ are each a hydrogen atom and the main product of the reaction is a 1-monoamine of the formula (III)

$$HR^1R^2C\text{—}C(NH_2)H_2 \qquad (III).$$

4. A process as claimed in claim 1, wherein $R^1$, $R^3$, and $R^4$ are each a hydrocarbon radical and $R^2$ is a hydrogen atom and the main product of the reaction is a monoamine of the formula (IV)

$$HR^1(NH_2)C\text{—}CR^3R^4 \qquad (IV).$$

5. A process as claimed in claim 1 carried out in a single step.

6. A process as claimed in claim 1 carried out in two steps in which
   the epoxide is reacted with ammonia in the absence of hydrogen to form the amino alcohol in a first step and
   the amino alcohol is reacted with ammonia and hydrogen to give the amine in a second step.

7. A process as claimed in claim 1, wherein the hydrocarbon radical is a $C_2$–$C_{30}$-hydrocarbon radical.

8. A process as claimed in claim 1, wherein the hydrocarbon radical is a linear alkyl radical.

9. A process as claimed in claim 1, wherein the reaction temperature is from 100 to 300° C.

10. A process as claimed in claim 1, wherein the reaction is carried out in THF as solvent.

* * * * *